United States Patent [19]

Collins

[11] 4,412,026
[45] Oct. 25, 1983

[54] ALDEHYDIC COMPOSITIONS

[75] Inventor: Forrest L. Collins, Minnetonka, Minn.

[73] Assignee: Henkel Corporation, Minneapolis, Minn.

[21] Appl. No.: 284,146

[22] Filed: Jul. 16, 1981

[51] Int. Cl.$^3$ .............................................. C08K 5/07
[52] U.S. Cl. .................................... 524/354; 524/547
[58] Field of Search .................. 260/29.65 Q, 32.8 R; 524/354

[56] References Cited

U.S. PATENT DOCUMENTS 3,931,089  1/1976  Karl .............................. 260/29.6 H
4,065,422  12/1977  Lundmark et al. ............ 260/29.6 E

OTHER PUBLICATIONS

Lange's Handbook of Chemistry, pp. 7–228, 229, 7–56, 57, 7–236, 237.

Primary Examiner—Joseph L. Schofer
Assistant Examiner—N. Sarofim
Attorney, Agent, or Firm—Forrest L. Collins

[57] ABSTRACT

An aldehyde containing composition is thickened by use of a polymer.

12 Claims, No Drawings

ALDEHYDIC COMPOSITIONS

BACKGROUND OF THE INVENTION

1. Field of the Invention

The present invention describes methods for increasing the viscosity of an aldehydic composition.

2. Description of the Art Practices

It is known from U.S. Pat. No. 3,931,089 issued Jan. 6, 1976 to Karl et al that acid solutions containing homopolymers of 2-acrylamido-2-methylpropanesulfonic acid and its salts may be used to thicken aqueous solutions. Such compositions were described as being useful in the controlled release of viscous acidic liquids, such as retarding the action of acids on limestone during acidizing of oil wells.

It was later discovered by Lundmark et al in U.S. Pat. No. 4,065,422 issued Dec. 27, 1977 that homopolymers of 2-acrylamido-2-methylpropanesulfonic acid salts could be used to impart lubricity to kerationous substrates such as skin or hair or upon mucous membranes to impart a lubricated feel. Such compositions were stated to have utility in diverse personal care products such as hand and body creams, soap bars, suntan lotion, preelectric shave skin conditioners aftershave lotions, lip balms, cold creams, bubble baths, cleansing and lotion pads, douches and vaginal lubricants. Similar products are described in U.S. Pat. No. 4,065,422 issued Dec. 27, 1977 to the same Lundmark et al entity comprising as an additional ingredient a monohydric alcohol. Such compositions were desirable where it was necessary to thicken an alcohol containing product to obtain the proper viscosity for the desired use.

It has now been found that if an aldehyde is dissolved in a miscible solvent which is compatible with a homopolymer of a salt of 2-acrylamido-2-methylpropane-sulfonic acid that an aldehyde will be obtained in a thickened solution by raising the viscosity of the dispersion containing the aldehyde. This is particularly important in applications where the aldehyde functions best by slow release such as in a disinfectant.

Therefore, there exists a need to prepare a thickened aldehyde containing composition. During the course of making the present invention, the author has discovered that various aldehydes have their viscosity raised substantially when included in a solution in which the aldehyde is miscible with the polymer of the present invention.

Throughout the specification and claims, percentages and ratios are by weight and temperatures are given in degrees Celsius unless otherwise indicated. The reader is also referred to the copending application of Bator et al Ser. No. 284,145 filed July 16, 1981 for thickened ketone compositions.

SUMMARY OF THE INVENTION

A composition having an aldehyde in a thickened state comprising:

(a) a low viscosity aldehyde
(b) a solvent in which the aldehyde is miscible selected from the group consisting of water and alcohols and mixtures thereof; and
(c) a homopolymeric salt of 2-acrylamido-2-methylpropanesulfonic acid in a amount sufficient to thicken the composition.

DETAILED DESCRIPTION OF THE INVENTION

The present invention first requires a salt of 2-acrylamido-2-methylpropanesulfonic acid. Such polymers are adequately described in U.S. Pat. No. 4,065,422 which is herein incorporated by reference together with the previously cited art.

In particular, the polymer is prepared by obtaining a monomer having the formula

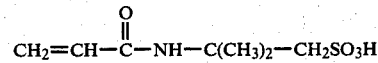

The polymerization reaction may be accomplished by solution, emulsion or suspension polymerization processes. The medium for the polymerization is conveniently water, the monohydric alcohol, or a mixture thereof. The choice of the medium is best dictated by the requirements of the end product to be formulated.

The polymerization reaction is described as temperature, pH, and catalyst sensitive. In addition it is desirable to exclude oxygen from the reaction vessel used to form the polymer as that material inhibits the polymerization process. The catalysts which are included to enhance the rate of polymerization are materials such as ammonium bisulfite, ferrous sulfate, hydrogen peroxide, sodium metabisulfite, or other redox catalysts.

The polymer may be varied in molecular weight by controlling the amount of the catalyst, the pH, or the rate of addition of the monomer to the reaction vessel. The polymerization may be facilitated by converting the monomer from its acid form to a salt which is water-soluble. This step is quite desirable in that one application of the present invention concerns personal care products where the treated skin requires that the pH of the personal care product be non-irritating. That is, the in use pH of the personal care product should be from about 3 to about 10, preferably about 4.5 to about 9.0 and most preferably from about 5 to about 8. Thus within the foregoing ranges some of the polymer may be in the acid form. The salts of the polymer preferably contain as cations, sodium, potassium, ammonium, monoethanolamine, diethanolamine, triethanolamine and 2-amino-2-methyl-1-propanol as well as mixtures thereof. The foregoing list is merely exemplary of salts which may be used. Also within the scope of the present invention are water-insoluble salts where the product is not adversely affected by precipitation of the polymer. Such products where water-insoluble salts of the polymer may be utilized are soap bars, or substantially non-aqueous products such as body lotions. Examples of suitable water-insoluble salts are the calcium and magnesium salts.

As was previously mentioned the molecular weight of the polymer may be controlled by the pH, the rate of addition of the monomer or the judicious use of the catalyst. It has been found desirable to utilize the aforedescribed polymers having a molecular weight from about 1,000,000 to about 5,000,000 more preferably from about 2,500,000 to about 4,500,000 to increase the asthetics of personal care composition. That is, it has been found that extremely high molecular weight polymers of the type described may result in a pituitive or stringly consistency of the end product. It has therefore been found desirable to limit the pituitivness by selecting the preferred molecular weight range. To this end any common chain transfer agent such as mercaptosuccinic acid may be used to limit the molecular weight of the polymer.

It is noted that the terminal groups on the polymer have little bearing on the desired properties of the products and are thus not specified. In the interest of complete disclosure it is noted that the terminal groups are most often hydrogen, but may also be hydroxyl, sulfate, sulfonate or

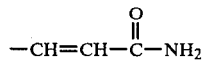

The next element of the present invention is the aldehyde which is to be thickened. It is first noted that it is somewhat surprising in that the aldehyde alone when mixed with the polymer causes the polymer to precipitate out. Thus, the effectiveness of the polymer as a thickening agent is lost. It was somewhat surprisingly found that tertiary mixtures of the aldehyde, polymer and water and/or alcohol as later described perform eminently well.

The aldehydes which are suggested for use in the present invention are those including formaldehyde, acetaldehyde, 2-methylpropenal, cyclopropylmethanal, propinaldehyde, crotonaldehyde, butyraldehyde and isobutyraldehyde. Glyoxal, a dialdehyde, is found to be useful in the present invention. Aldehydes may be used as long as they are liquid or dispersable in the later described solvent.

The solvent utilized in the present invention is conveniently water or alcohol or mixtures thereof. The alcohols are preferably lower alcohols such as: methanol, ethanol, n-propanol, isopropanol and the like. It is of course also possible to include the higher alcohols such as lauryl, myristyl, cetyl and stearyl as well as unsaturated alcohols such as oleyl. It is also possible to vary the mixtures so that water and alcohol mixtures are used. Occasionally, additional solubilizing agents are required where the higher normally solid aldehydes are employed.

The products of the present invention are formulated by simply combining the various ingredients in the amounts desired and thereafter by thoroughly mixing the components.

The preferred amounts of the components of the present invention are from about 5 percent to about 50 percent, preferably from about 10 percent to about 40 percent by weight of the aldehyde. The solvent is present at from about 20 percent to about 80 percent by weight, preferably from about 25 percent to about 75 percent by weight. The polymer of the 2-acrylamido-2-methylpropanesulfonic acid salt is present at from about 0.25 percent to about 5 percent, preferably from about 0.4 percent to about 4.0 percent by weight.

The following are examples of the present invention.

EXAMPLE I

| HSP* 1180 | 13.3 grams |
|---|---|
| 37% formaldehyde in water | 386.67 grams |
| | #2 Brookfield viscosity at 2.5 rpms |
| | 336 cps |

*0.5 percent solids in the finished product. HSP 1180 is the aforedescribed polymer available from the Henkel Corporation.

EXAMPLE II

| | % |
|---|---|
| HSP 1180 | 0.5 |
| Benzaldehyde | 10.0 |
| Isopropanol | 89.5 |
| | viscosity suitable |

EXAMPLE III

| HSP 1180 | 13.33 grams |
|---|---|
| Glyoxal (40% in H₂O) | 386.67 grams |
| | viscosity 2.5 rpm Brookfield #2 |
| | 1056 cps |

This example may be repeated using the alcohols mentioned in the specification as well as alcohol-water mixtures.

EXAMPLE IV

| | % |
|---|---|
| HSP 1180 | 0.5 |
| 10% solids acetaldehyde in water | 10.0 |
| H₂O q.s. | 89.5 |
| | viscosity on #2 Brookfield at 2.5 rpms |
| | 220 cps |

What is claimed is:

1. A personal care or disinfectant product composition having an aldehyde in a thickened state comprising:
   (a) a low viscosity aldehyde;
   (b) a solvent in which the aldehyde is miscible selected from the group consisting of water and alcohols and mixtures thereof; and
   (c) a homopolymeric salt of 2-acrylamido-2-methylpropanesulfonic acid in an amount to sufficient to thicken the composition.

2. The composition of claim 1 containing from about 0.25 percent to about 5 percent by weight of component (c).

3. The composition of claim 1 wherein component (b) is a lower alcohol containing from about 1 to about 4 carbon atoms.

4. The composition of claim 1 containing from about 5 percent to about 50 percent by weight of component (a).

5. The composition of claim 2 containing from about 0.4 percent to about 4 percent by weight of component (c).

6. The composition of claim 1 wherein component (b) is water.

7. The composition of claim 3 wherein component (b) is ethanol.

8. The composition of claim 1 wherein the aldehyde is selected from the group consisting of formaldehyde, acetaldehyde and glyoxal.

9. The composition of claim 1 wherein component (b) is present at from about 20 percent to about 80 percent by weight.

10. The composition of claim 1 wherein component (c) has a molecular weight of from about 1 million to about 5 million.

11. A process for disinfecting an article by applying a composition comprising:

(a) a low viscosity aldehyde;
(b) a solvent in which the formaldehyde is miscible selected from the group consisting of water and alcohols and mixtures thereof; and
(c) a homopolymeric salt of 2-acrylamido-2-methyl-propanesulfonic acid in an amount to sufficient to thicken the composition, wherein said article is disinfected through the slow release of the aldehyde in said composition.

12. A disinfectant composition having formaldehyde in a thickened state comprising:
(a) formaldehyde;
(b) a solvent in which the formaldehyde is miscible selected from the group consisting of water and alcohols and mixtures thereof; and
(c) a homopolymeric sale of 2-acrylamido-2-methyl-propanesulfonic acid in an amount to sufficient to thicken the composition.

* * * * *